United States Patent
Headstrom et al.

(10) Patent No.: US 8,863,346 B2
(45) Date of Patent: Oct. 21, 2014

(54) HANDS-FREE ORAL CLEANING APPLIANCE

(75) Inventors: Patrick A. Headstrom, Seattle, WA (US); Tijn Pieter Lodewijk Huttenhuis, Seattle, WA (US); Jeffrey Daniel Allison, Lake Oswego, OR (US); Lawrence David Azzano, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 29 days.

(21) Appl. No.: 13/390,165

(22) PCT Filed: Jun. 16, 2010

(86) PCT No.: PCT/IB2010/052709
§ 371 (c)(1),
(2), (4) Date: Feb. 13, 2012

(87) PCT Pub. No.: WO2011/021109
PCT Pub. Date: Feb. 24, 2011

(65) Prior Publication Data
US 2012/0141954 A1 Jun. 7, 2012

Related U.S. Application Data

(60) Provisional application No. 61/235,031, filed on Aug. 19, 2009.

(51) Int. Cl.
A61C 17/20 (2006.01)
A61C 17/22 (2006.01)
A61C 17/34 (2006.01)

(52) U.S. Cl.
CPC ........... *A61C 17/3481* (2013.01); *A61C 17/228* (2013.01)

USPC .............................. 15/167.1; 15/22.1; 15/21.1

(58) Field of Classification Search
USPC ........................... 15/22.1, 167.1; 433/103, 25
See application file for complete search history.

(56) References Cited

U.S. PATENT DOCUMENTS

| 4,224,710 A * | 9/1980 | Solow ............................ 15/22.1 |
| 4,292,705 A | 10/1981 | Stouffer |
| 4,585,416 A | 4/1986 | De Niro et al. |
| 5,337,435 A * | 8/1994 | Krasner et al. ..................... 15/23 |
| 6,152,733 A | 11/2000 | Hegemann et al. |
| 8,241,035 B2 * | 8/2012 | Jones et al. ...................... 433/29 |
| 2007/0259310 A1 | 11/2007 | Goodson et al. |

FOREIGN PATENT DOCUMENTS

| FR | 2860973 A1 | 4/2005 |
| GB | 2327339 A | 1/1999 |
| WO | 0247512 A1 | 6/2002 |

* cited by examiner

*Primary Examiner* — Monica Carter
*Assistant Examiner* — Stephanie Berry (57) ABSTRACT

The hands-free dental appliance includes upper and lower tray members (12, 14) for receiving the teeth of the user, the tray members having teeth contact members such as bristles. A power assembly (28) moves the tray member in a reciprocal manner, resulting in cleaning of the surfaces of the teeth by the bristles. A grounding system (30) with bite portions (32, 34, 36) for biting contact whereby the user's teeth grounds the appliance to the user's mouth structure, reacting both static and dynamic forces, the grounding system being either separate from the tray members or flexibly connected to the tray members, allowing the tray members to move and clean the teeth without the user having to hold or otherwise manipulate the appliance.

11 Claims, 6 Drawing Sheets

HANDS-FREE ORAL CLEANING APPLIANCE

This invention relates generally to oral cleaning appliances, including mouthpieces, and more specifically concerns such an appliance which is arranged to transfer static and dynamic forces of the appliance into the user's mouth structure.

Oral cleaning appliances, including both toothbrushes and mouthpieces, are typically hand-held and manipulated by hand to accomplish the desired cleaning. The user will position the appliance such that the cleaning elements are positioned in the mouth and then will maneuver the cleaning elements around the teeth by arm and hand action. Effective cleaning of the teeth thus requires appropriate technique by the user. The user's hand is required to both support and transfer the weight of the handle and also the cleaning force reaction to ground or to the user's body.

Accordingly, it would be desirable to have an appliance which is essentially hands-free, eliminating the need for the user to use their hands during the teeth-cleaning event, allowing the hands for use for other tasks, and also resulting in the appliance being independent of the user's technique, since the user does not have to manipulate the device in a particular manner to produce the desired cleaning.

Accordingly, the hands-free dental appliance comprises: a mouthpiece assembly for receiving teeth having a contact system for cleaning the surfaces of the teeth of a user; a power assembly which, when activated, operates the receiving assembly so as to produce movement of the contact system to clean the surfaces of the teeth; and a system which is part of the appliance for grounding the appliance to the user's mouth or head structure, allowing the mouthpiece assembly to operate to produce cleaning of the teeth without the user having to hold or manipulate the appliance.

Several embodiments of a dental cleaning appliance configured for hands-free operation are shown and described herein. Each embodiment includes a particular structure to (1) transfer the weight of the appliance into the user's jaw and skull structure, referred to as the static mode of the appliance, and (2) to react or transfer the resultant force vectors from the cleaning action of the appliance into the user's jaw and skull structure, referred to as the dynamic load of the appliance.

Figure 1:
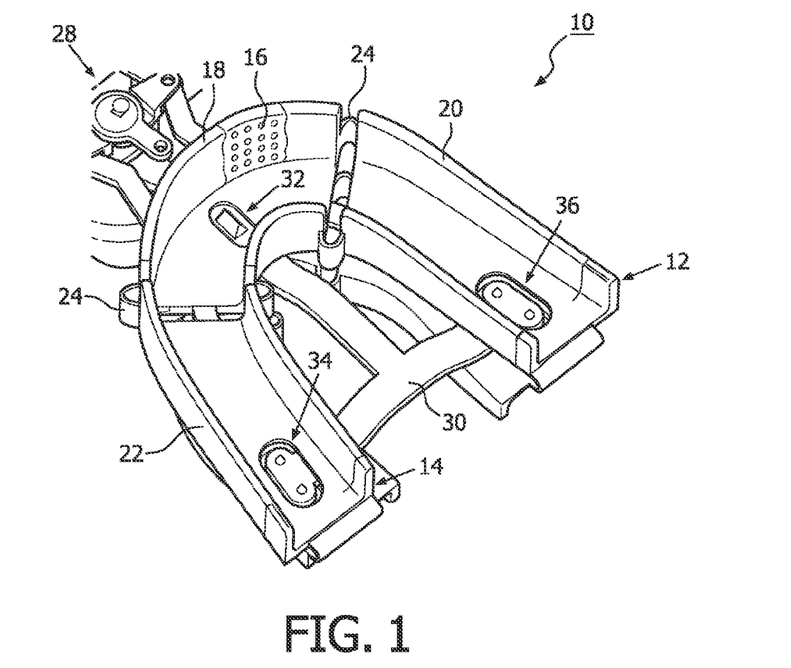
FIG. 1 is a perspective view of a first embodiment of the present invention.
Figure 2:
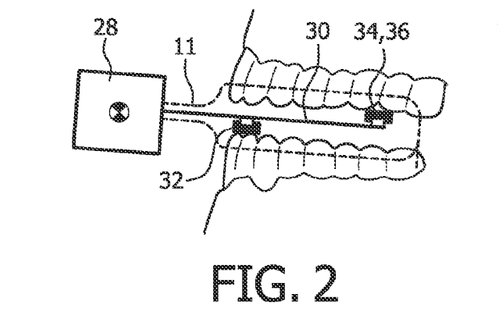
FIG. 2 is a simplified side elevational view of the appliance of FIG. 1 positioned for use.
Figure 3:
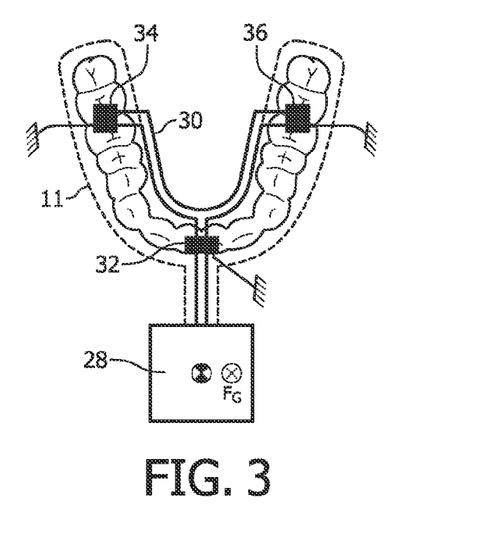
FIG. 3 is a top view of the appliance of FIG. 1 positioned for use.

FIGS. 1-3 show a first embodiment of the appliance. The appliance, referred to generally at 10, is in the form of a mouthpiece 11 having upper and lower teeth-receiving members 12 and 14, referred to as trays, which are configured to receive the teeth in the upper and lower jaws (maxilla and mandible) of the user. It should be understood, however, that the term mouthpiece as used herein can receive and be adapted to clean a complete set of teeth or a partial set of teeth, even a single tooth. The invention is thus not limited to a complete or full mouthpiece, but includes partial mouthpieces as well. Tray members 12 and 14 are conventional in their structure. They cover the occlusal regions of the teeth and also at least a portion of the side surfaces of the teeth. The tray members include various cleansing media, such as bristles 16 (partially shown in FIG. 1) or other elements which produce a scrubbing action when the appliance is activated.

In the embodiment shown, each tray member is divided into three sections 18, 20 and 22, which may be connected by flexible web elements 24. Section 18 covers generally the incisor (front) portion of the teeth, while opposing sections 20 and 22 cover the molar (rear) portions of the teeth. In the embodiment shown, tray members 12 and 14 are moved back and forth by a drive train assembly 28. Drive train assembly 28 can include a motor or other drive system for moving the tray members back and forth in a reciprocal action to produce a scrubbing action on the teeth by the bristles 16 or other cleaning members positioned on the individual tray members. Alternative cleaning arrangements to scrubbing can also be used; for instance, a bladder member supported on the tray elements, which can be alternately inflated and deflated with bristles mounted thereon moving toward and away from the teeth to produce the desired cleansing action. The drive train assembly can be located exterior to the mouth or inside the mouth.

In addition to the tray members, appliance 10 in FIGS. 1-3 includes a static frame assembly 30, also referred to as a grounding frame, which is rigidly connected to the drive train housing. In the embodiment shown, frame assembly 30 is in the form a "T", with three bite members for fixed contact with the teeth. One bite member 32 extends downwardly from the frame assembly at the front of the mouth to contact the mandible incisors, and two other spaced-apart bite members 34 and 36 extend through openings in upper tray 12 near the rear of the mouth for contact with the maxilla molars of the jaw. In the embodiment shown, the bite members are generally oval in configuration and of a size to approximately mate with the occlusal portions of those teeth which they are contacting. The bite elements are made of silicone material so as to permit the user to firmly grip the bite members with their teeth.

In operation, the user bites down on the three bite members, to provide a stable position for the appliance in the mouth. The tray members are free to move and do so when the drive train is activated to produce the desired cleaning, by scrubbing or other means. While the embodiment shown has three bite members, one for incisors and two for molars, the bite members can be in other positions and may include more or sometimes fewer than three members.

FIGS. 4-13 show a second embodiment of the oral cleaning appliance. The second embodiment includes a drive train 40 and a teeth-receiving mouthpiece 42 (such as two tray members), which are similar to that shown for the first embodiment and are hence not explained in detail relative to this embodiment. Instead of a separate rigid frame member, however, to ground the appliance, the second embodiment uses an elastic coupling arrangement to accomplish the desired grounding, i.e. the transfer of the static and dynamic forces of the appliance to the jaw and/or skull of the user. One variation of the elastic coupling embodiment includes several bite pads 46 (FIG. 7) which are positioned, respectively, in corresponding openings 48 in each of the tray members 50, with bite pads 46 being connected directly to the tray members via a flexible or elastic web 49. This variation is shown in FIGS. 4-5 and 7-9. Generally, bite pads 46 will be positioned so that physical contact is made by the teeth with the incisors and the molars similar to that for the first embodiment above.

Figure 4:
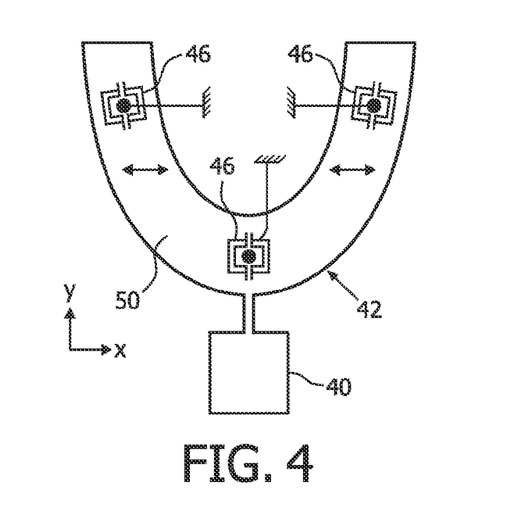
FIGS. 4, 5 and 6 are simplified top views showing variations of a second embodiment.
Figure 5:
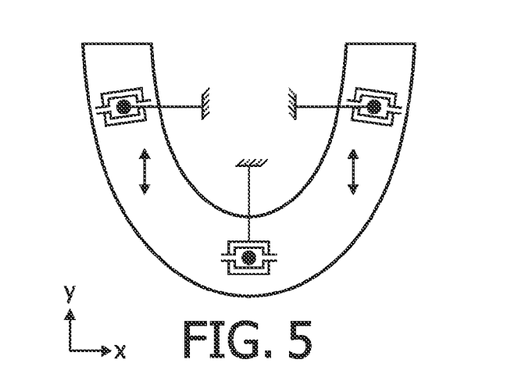
Figure 8:
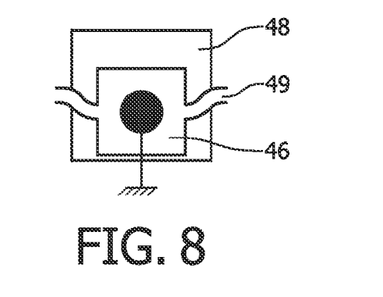
FIGS. 8 and 9 are top views of the selected portion of FIG. 7.
Figure 9:
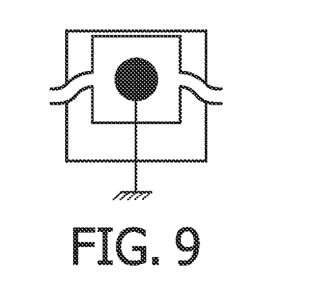

In this embodiment, bite pads 46 are made from silicone material, while the connecting web elements 49 are made from silicone or plastic material. Typically, the web elements connect the opposing sides of the bite pads to the tray members. The bite pads are generally square, approximately 5 mm×5 mm, while the connecting web elements are approximately 1.0 mm wide and extend across open space 48 between the bite pads and the tray member 50. As one example, the spacing between the bite pads 46 and the surrounding tray is approximately 1 mm. The web elements 49 may be oriented in different directions so as to facilitate a particular motion of the tray, i.e. side-to-side or front-to-back, as shown in FIGS. 4 and 5, respectively. In operation, web elements 49 will flex and stretch as the tray members are moved, so that the bite pads will move back and forth within the opening, as illustrated in FIGS. 8 and 9.

Figure 6:
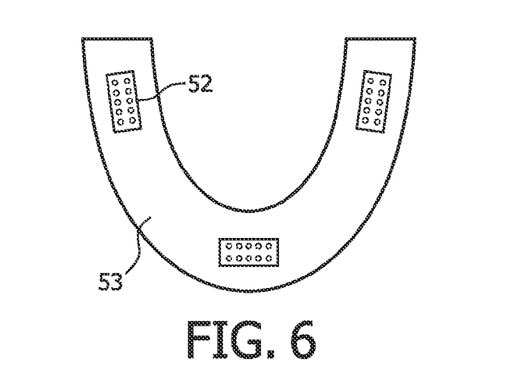
Figure 7:
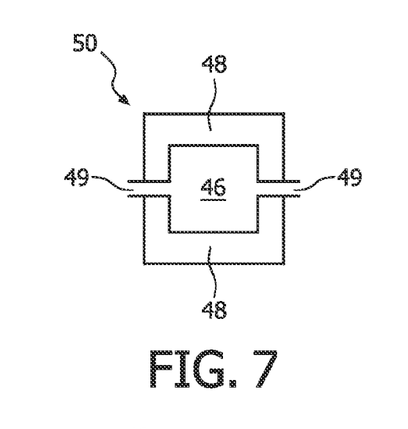
FIG. 7 is a top view of a selected portion of one variation of the second embodiment.

FIG. 6 shows an arrangement by which the elastic coupling is accomplished with bristles or other flexible protrusions. In particular, coupling bristle portions 52 are secured to the occlusal surfaces of the tray members 53, and are configured and arranged so that the user bites down on the coupling bristle portions 52, while tray members 53 with the scrubbing bristles move back and forth, cleaning the teeth. The coupling bristle portions 52 provide an elastic coupling function which reacts the static and dynamic loads to the jaw and skull of the user.

Figure 10:
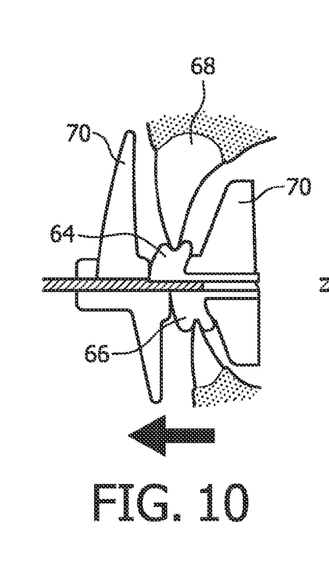
FIGS. 10, 11 and 12 are side views showing the operation of another variation of the second embodiment.
Figure 11:
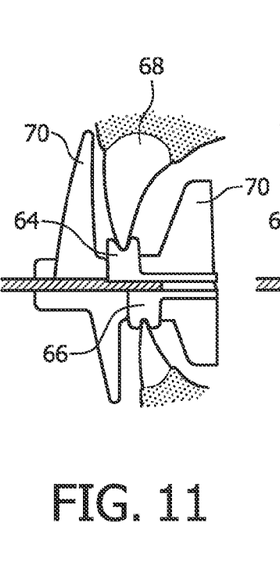
Figure 12:
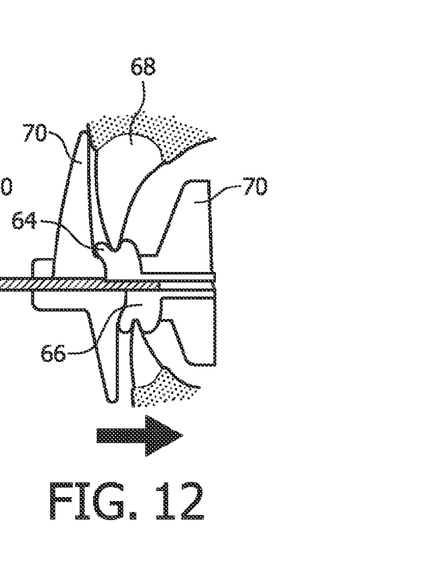
Figures 13, 14:
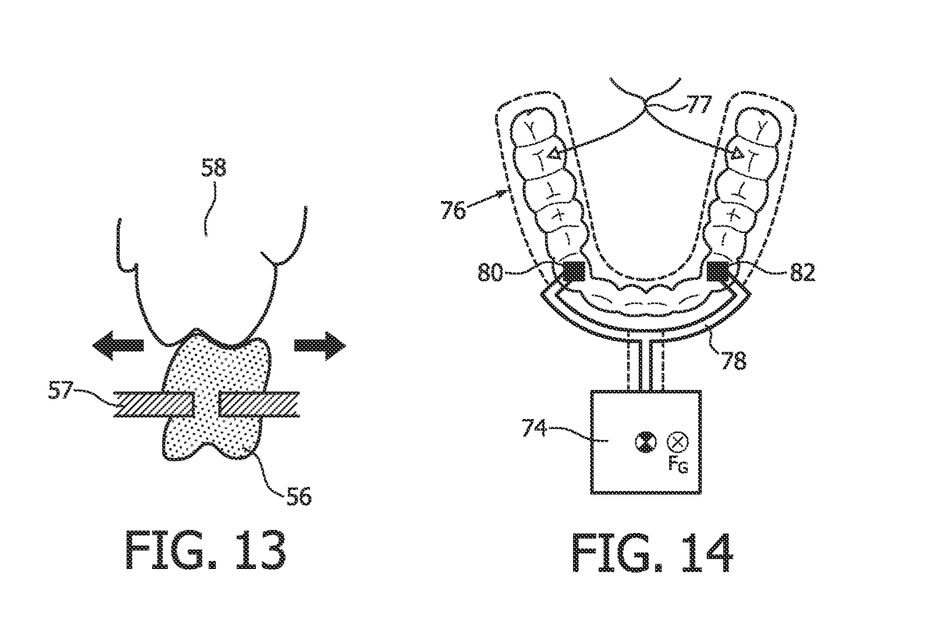
FIG. 13 is a simplified elevational view of another variation of one portion of the second embodiment.
FIG. 14 is a top view of a third embodiment of the present invention, combining the first and second embodiments, positioned for use.

FIGS. 10-13 show an elastic coupling arrangement in which the bite pad members are made from flexible or elastic material, such as silicone. Thus, as tray members move back and forth, the bite pads in this arrangement distort, resulting in the teeth maintaining their original position, while the tray members with the brushing elements move back and forth across the tooth surfaces, producing the cleaning. FIG. 13 is a simplified view showing such an arrangement involving such isolators used with molars. Bite pad 56 is molded or secured to the tray member 57. The user bites down, with molars 58 contacting the flexible bite pads 56. This concept involving a flexible bite pad is shown more clearly in FIGS. 10-12, which are for incisor teeth. In those figures, upper and lower bite pads are shown at 64 and 66. The incisor teeth are shown generally at 68, while the brushing elements are shown generally at 70. As the tray members with the brushing elements move back and forth in a reciprocating action between a forward position, a neutral position and a rear position, as shown in FIGS. 10, 11 and 12, respectively, the upper and lower bite pads 64, 66 distort first in one direction, then back to neutral, and then in the other direction. The incisors remain in their original position, while the brushing elements move back and forth relative to the teeth, producing the desired cleansing action. The static and dynamic loads created by the appliance are both transferred to the user's jaw and skull structure FIG. 14 shows a third embodiment, which is a combination of the first and second embodiments. In this embodiment, a drive train 74, which again can be arranged to be inside or outside of the mouth, drives the tray members, shown as a unit at 76. Tray members 76, as noted above, can take a variety of arrangements and configurations for cleansing of the teeth. The embodiment includes a static frame assembly 78 like FIG. 1, fixedly attached to a part of the drive train assembly, such as the housing thereof, the frame assembly including two static bite pads 80 and 82 which are arranged in position to contact opposing incisors of the teeth, typically the mandible teeth. It should be understood, however, that other arrangements, such as a single bite pad located at the mid-portion of the set of teeth, can be used.

The molar connections in this embodiment are grounded through elastic coupling members, such as in the second embodiment discussed above. Typically, the elastic coupling members will be on opposite sides of the jaw for contact with either the mandible or maxilla molars, such as at 77. These elastic coupling members can be bristles, separate bite island isolators, or flexible bite members, as discussed above.

Figure 15:
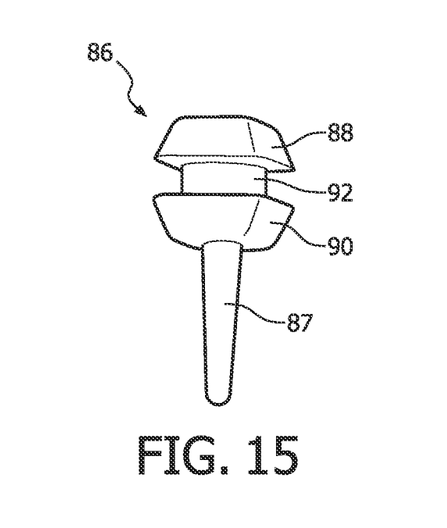
FIG. 15 is an elevational view of an element which is useful in the first, second and third embodiments.

For the second and third embodiments described above, when bristles are used for the elastic coupling members, it is important that the molars do not engage, i.e. contact, the mouthpiece members, e.g. the individual tray members, while those bristles on the tray member designed for cleaning of the teeth are allowed a good reach. One solution is to provide a small silicon isolation grounding pad 86 (FIG. 15) as a part of the bristle coupling structure. Pad 86 is installed by drilling a hole through the occlusal surface of the mouthpiece trays, removing the coupling bristles in that part, pulling the grounding pad 86 through the hole, and then trimming the resulting installation tail 87. The ground pad includes two layers 88 and 90, an intermediate joining portion 92 and tail section 87. The silicon grounding pad 86 is of relatively soft silicon, such as Shore A15-30, allowing the mounting pad to be pulled through the opening in the tray member, so that the tray member is held between layers 88 and 90. The mounting pad 86 maintains the required isolating transfer function of a hands-free appliance.

Figure 16:
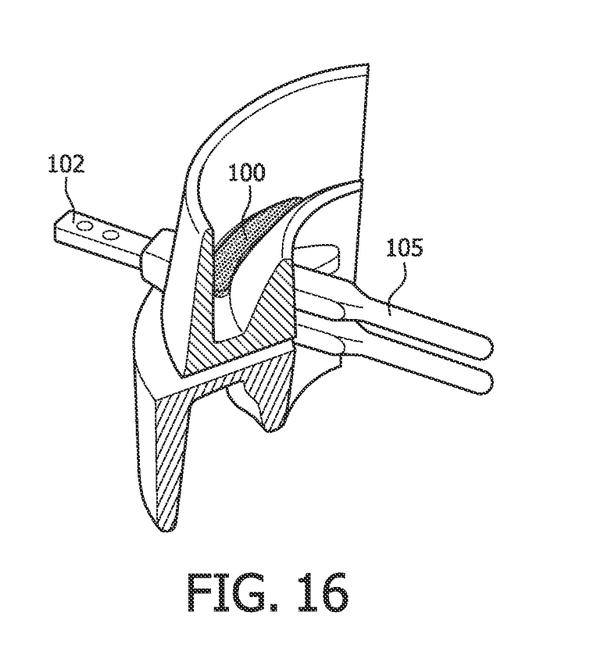
FIGS. 16 and 17 are perspective views of a portion of the second or third embodiments.
Figure 17:
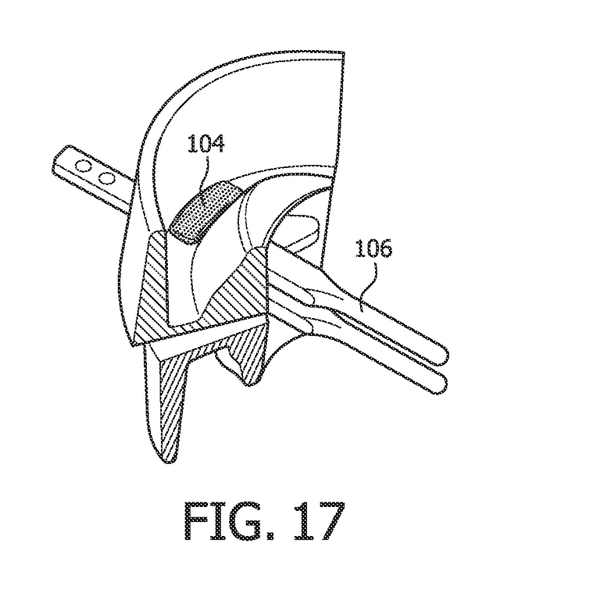

FIGS. 16 and 17 show particular incisor isolator/grounding members when bristles are used as elastic coupling members. It is recognized that bristles alone may not be able to fully react the load at the mandible incisors in some circumstances. Incisors are relatively sharp and hence may displace the coupling bristles, allowing the teeth to directly contact the tray members which, as indicated above, is undesirable, since the tray members are then prevented from moving. This is potentially hazardous to the user when the drive train is turned on. The elements of FIGS. 16 and 17 show members designed to prevent tooth-to-tray contact. Two soft silicone isolation parts can be added to prevent coupling of the incisors to the front portion of the trays. FIGS. 16 and 17 show the assembly with both the mandible and maxilla isolators on opposing sides thereof, FIG. 16 shows the mandible isolator in the upper position for ease of viewing, while FIG. 17 shows the unit flipped over so that the maxilla isolator is in the upper position. Element 102 connected to the drive train. In FIG. 16, the majority of the weight of the mechanism will be reacted by this isolator. Isolator element 100 is relatively wide and covers the entire occlusal surface. Isolator 100 includes an extending arm 105 which fits into and is held in a small recess in the occlusal surface of the front portion of the trays. The mandible incisors support the mandible isolator which, due to its low durometer, will flex as the trays are translated back and forth to clean the teeth.

The durometer is relatively low (Shore A15) so that the isolator can bend easily and keep the drive train loads low. If the isolator material is too soft, the incisors might compress them until they no longer remain apart from the occlusal surface of the trays. The compressed height of the isolator should be approximately one-third of the actual bristle height above the bristle backing material.

Isolator 104 on the maxilla (upper jaw) side (FIG. 17) does not experience the same magnitude of vertical loads and hence can be shorter. Isolator 104 includes an extending arm 106 which fits into the tray member. Isolator 104 acts more like a bite stopper than as a ground for the appliance and can be designed with a nominal height which is equal to one-third of the bristle length above the bristle backing material.

Typically, the isolators of FIGS. 16 and 17 will be molded separately and assembled into recesses in the front part of the mouthpiece tray members. The isolators will typically have a "T" shape with an extra long extending arms 105, 106 to simplify assembly. The installation of these isolators can occur either before or after the application of the bristles to the tray members. After installation through the tray member lingual walls, any excess leg portion can be trimmed, once the isolator is seated correctly. Alternatively, the isolators could be molded as part of the front of the tray members. In either case, the bristle field for cleansing will need to avoid the recesses to allow room for the isolator members.

Figure 18:
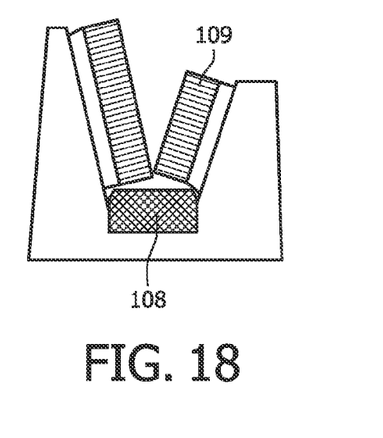
FIG. 18 is a simplified cross-sectional view of an alternative portion of the second embodiment.

Alternatively, as shown in FIG. 18, the isolator member 108 can be arranged so that the bristle field 109 on the tray members partially covers the isolator member 108.

Figure 19:
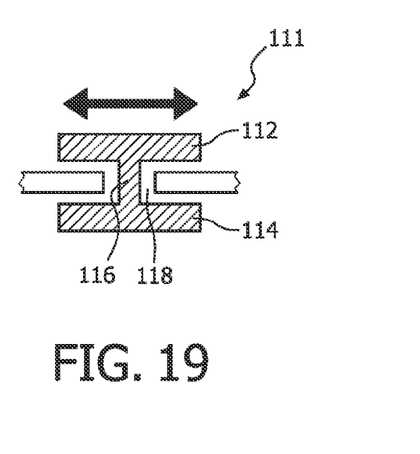
FIG. 19 is a simplified cross-sectional view of a portion of a fourth embodiment of the present invention.
Figure 20:
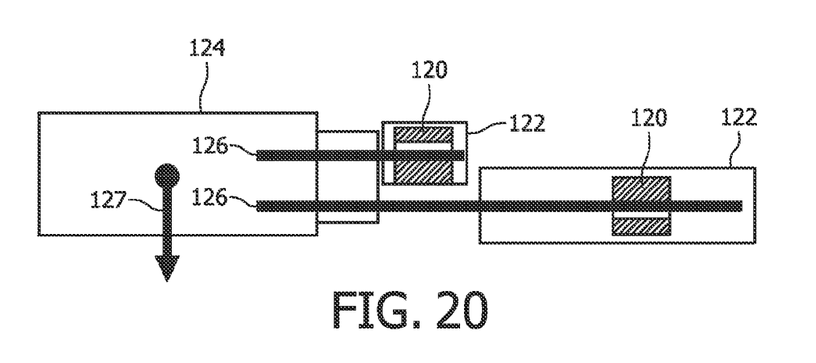
FIGS. 20 and 21 are side elevational views showing in more detail the fourth embodiment.
Figure 21:
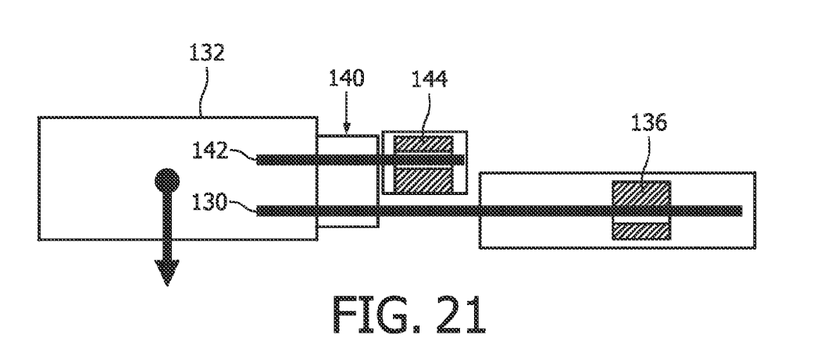

A fourth embodiment is shown in FIGS. 19-21. This embodiment uses slider bearings which are mounted for sliding action on slide bearing arms which connect the drive train of the appliance to the teeth-receiving tray members. The tray members thus can be moved back and forth while the teeth are maintained in place by the user biting down on the slider bearings. A slider bearing is shown in FIG. 19. The slider bearing includes two opposing elements 112 and 114 joined by an intermediate member 116. The slider bearings function as grounding pads upon which the teeth meet. The slider bearings and the teeth remain in place, providing support for the appliance, while the tray members move back and forth by action of the drive train. This arrangement results in the vertical loads being transferred but not the side-to-side loads. In the embodiment shown, the slider members are made from plastic or silicone material.

FIG. 20 shows one embodiment in which slider bearings 120 are positioned for both the molar and the incisor teeth. The tray members 122 are connected to a drive train 124 by bearing arms 126. The vertical weight of the handle, represented by arrow 127, is reacted by this arrangement. In operation, the bearing arms 126 and the tray members move back and forth, sliding relative to the fixed bearings 120 and the teeth. The movement of the trays produces cleansing of the teeth.

FIG. 21 shows a slightly different arrangement. Slider arms 130 connect the drive train 132 to the trays for the molars, and there is a sliding action between bearing pads 136 and the slider arms for the molars. The molar bite pads transfer the forces to the housing by sliding on the slider arms 130. For the incisors, there is support for the weight of the appliance by a lip support member 140, which supports slider arm 142 upon which slider bearing pad 144 slides. The front vertical reaction is created by support member 140.

It should be understood that the above-described embodiments could be adapted so that other parts of the mouth and head structure provide grounding support for the appliance. This could include, for instance, the roof of the mouth and the chin of the user. It could also be the forehead.

Hence, a hands-free dental cleaning appliance has been designed which reacts or transfers both static and dynamic loads from the appliance into the jaw and head structure of the user. This is accomplished in a number of different embodiments. The various embodiments permit the user to operate the appliance without the necessity of hand support and maneuvering of the appliance, such that cleaning becomes independent of user action.

Although a number of embodiments of the invention have been disclosed for purposes of illustration, it should be understood that additional embodiments can be used without departing from the spirit of the invention, which is defined by the claims which follow.

The invention claimed is:
1. A hands-free dental appliance, comprising:
 a mouthpiece assembly (1) for receiving teeth having a contact system for cleaning the surfaces of the teeth of a user;
 a power assembly (28) which, when activated, operates the mouthpiece assembly so as to produce movement of the contact system to clean the surfaces of the teeth; and
 a system (30) which is part of the appliance for grounding the appliance to the user's mouth or head structure, providing a stable position of the appliance in the mouth while allowing the mouthpiece assembly to move to produce cleaning of the teeth without the user having to hold or manipulate the appliance, wherein the grounding system includes a static frame member (30) with bite portions (32, 34, 36) for direct contact with the teeth, the static frame being separate from the mouthpiece assembly and rigidly connected to the power assembly such that it does not move when the power assembly is activated for cleaning of the teeth.

2. The dental appliance of claim 1, wherein the contact system comprises teeth-cleaning bristles (16) mounted in the mouthpiece assembly.

3. The dental appliance of claim 2, wherein the mouthpiece assembly includes upper and lower teeth receiving tray members (12, 14) connected to the power assembly, which includes a motor for moving the tray members in reciprocating fashion to clean the teeth.

4. The dental appliance of claim 2, wherein the contact system is in a form of an inflatable bladder with bristles thereon and wherein the power assembly successively inflates and deflates the bladder, producing cleansing contact between the bristles on the bladder and the teeth.

5. The dental appliance of claim 1, wherein the bite portions include at least one bite portion positioned for contact with incisors in a vicinity of the front of the mouthpiece assembly, and two or more bite portions positioned for contact with molars toward a rear of the mouthpiece, wherein in operation, when the user bites down on the bite portions, the appliance is grounded to the mouth structure of the user, permitting the mouthpiece to clean the teeth hands-free.

6. The dental appliance of claim 5, wherein the bite portions for the incisors are positioned for contact with the mandible incisors, while the bite portions for the molars are positioned for contact with the maxilla molars.

7. The dental appliance of claim 1, wherein the static frame member (78) is configured so that the bite portions (80, 82) thereon contact incisors and wherein the grounding system further includes at least two elastic coupling members (77) positioned for contact with molars toward a rear of the mouthpiece.

8. A hands-free dental appliance, comprising:
 a mouthpiece assembly (1) for receiving teeth having a contact system for cleaning the surfaces of the teeth of a user, wherein the mouthpiece assembly includes upper and lower teeth receiving tray members (12, 14) connected to the power assembly, which includes a motor for moving the tray members in reciprocating fashion to clean the teeth;

a power assembly (28) which when activated operates the mouthpiece assembly so as to produce movement of the contact system to clean the surfaces of the teeth; and a system (30), which is part of the appliance, for grounding the appliance to the user's mouth or head structure, providing a stable position of the appliance in the mouth while allowing the mouthpiece assembly to move to produce cleaning of the teeth without the user having to hold or manipulate the appliance, wherein the grounding system includes a plurality of elastic coupling members (46) flexibly connected to, or themselves being flexible and connected to, the mouthpiece, the elastic coupling members being positioned to contact the user's incisors or molars or the user's incisors and molars, wherein the elastic coupling members comprise bite elements (46) for contact with selected teeth of the user, connected by flexible web members (49) to the frame members.

9. The dental appliance of claim 8, wherein the elastic coupling members are bristles (52).

10. A hands-free dental appliance, comprising:

a mouthpiece assembly (1) for receiving teeth having a contact system for cleaning the surfaces of the teeth of a user, wherein the mouthpiece assembly includes upper and lower teeth receiving tray members (12, 14) connected to the power assembly, which includes a motor for moving the tray members in reciprocating fashion to clean the teeth;

a power assembly (28) which, when activated, operates the workpiece assembly so as to produce a movement of the contact system to clean the surfaces of the teeth;

a system (30), which is part of the appliance, for grounding the appliance to the user's mouth or head structure, providing a stable position of the appliance in the mouth while allowing the mouthpiece assembly to move to produce cleaning of the teeth without the user having to hold or manipulate the appliance; and a plurality of slider bearings (10) slidably mounted on slider bearing arms (126) which are connected to the power assembly for back-and-forth movement of the tray members, wherein the slider bearings are positioned for biting contact with incisors and at least two opposing molars, such that the slider bearings and the teeth remain in place during movement of the tray members.

11. The dental appliance of claim 10, including a lip based supporting assembly (140) for a slider bearing arm (142) upon which the incisor slider bearing (144) is mounted.

* * * * *